(12) United States Patent
Wilson et al.

(10) Patent No.: US 12,128,039 B2
(45) Date of Patent: *Oct. 29, 2024

(54) PROCESSES FOR PREPARING QUINOLINE COMPOUNDS AND PHARMACEUTICAL COMPOSITIONS CONTAINING SUCH COMPOUNDS

(71) Applicant: Exelixis, Inc., Alameda, CA (US)

(72) Inventors: Jo Ann Wilson, San Francisco, CA (US); Khalid Shah, Half Moon Bay, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,836

(22) Filed: Feb. 8, 2024

(65) Prior Publication Data

US 2024/0189298 A1 Jun. 13, 2024

Related U.S. Application Data

(60) Continuation of application No. 18/462,739, filed on Sep. 7, 2023, which is a continuation of application No. 17/679,634, filed on Feb. 24, 2022, now abandoned, which is a continuation of application No. 17/170,275, filed on Feb. 8, 2021, now Pat. No. 11,298,349, which is a continuation of application No. 17/152,394, filed on Jan. 19, 2021, now abandoned, which is a continuation of application No. 16/706,323, filed on Dec. 6, 2019, now abandoned, which is a division of application No. 16/151,653, filed on Oct. 4, 2018, now Pat. No. 10,543,206, which is a division of application No. 15/348,716, filed on Nov. 10, 2016, now Pat. No. 10,123,999, which is a division of application No. 13/984,559, filed as application No. PCT/US2012/024591 on Feb. 10, 2012, now Pat. No. 9,717,720.

(60) Provisional application No. 61/441,520, filed on Feb. 10, 2011, provisional application No. 61/441,527, filed on Feb. 10, 2011.

(51) Int. Cl.
*A61K 31/47* (2006.01)
*C07D 215/233* (2006.01)

(52) U.S. Cl.
CPC .......... *A61K 31/47* (2013.01); *C07D 215/233* (2013.01)

(58) Field of Classification Search
CPC ........................ C07D 2158/233; A61K 31/47
See application file for complete search history.

(56) References Cited

U.S. PATENT DOCUMENTS

| | | | |
|---|---|---|---|
| 5,358,941 A | 10/1994 | Bechard et al. | |
| 6,030,643 A | 2/2000 | Adams et al. | |
| 7,166,722 B2 | 1/2007 | Matsunaga et al. | |
| 7,169,789 B2 | 1/2007 | Kubo et al. | |
| 7,579,473 B2 | 8/2009 | Bannen et al. | |
| 7,977,345 B2 | 7/2011 | Bannen et al. | |
| 7,999,006 B2 | 8/2011 | Lamb | |
| 8,067,436 B2 | 11/2011 | Bannen et al. | |
| 8,178,532 B2 | 5/2012 | Bannen et al. | |
| 8,314,232 B2 | 11/2012 | Deschamps et al. | |
| 8,476,298 B2 | 7/2013 | Bannen et al. | |
| 8,497,284 B2 | 7/2013 | Bannen et al. | |
| 8,673,912 B2 | 3/2014 | Cannon et al. | |
| 8,877,776 B2 * | 11/2014 | Brown | A61P 5/14 514/312 |
| 9,174,947 B2 | 11/2015 | Bannen et al. | |
| 9,365,516 B2 | 6/2016 | Wilson et al. | |
| 9,717,720 B2 * | 8/2017 | Wilson | A61K 31/47 |
| 9,724,342 B2 | 8/2017 | Wilson et al. | |
| 9,809,549 B2 | 11/2017 | Brown et al. | |
| 9,969,692 B2 | 5/2018 | Wilson et al. | |
| 10,034,873 B2 | 7/2018 | Wilson et al. | |
| 10,039,757 B2 | 9/2018 | Wilson et al. | |
| 10,123,999 B2 | 11/2018 | Wilson et al. | |
| 10,166,225 B2 | 1/2019 | Aftab et al. | |
| 11,091,439 B2 * | 8/2021 | Brown | A61P 5/14 |
| 11,091,440 B2 * | 8/2021 | Brown | A61P 43/00 |
| 11,098,015 B2 | 8/2021 | Brown et al. | |
| 11,298,349 B2 * | 4/2022 | Wilson | A61P 35/00 |
| 11,433,064 B2 * | 9/2022 | Aftab | A61K 45/06 |
| 11,504,362 B2 * | 11/2022 | Shah | A61K 9/0095 |
| 12,016,854 B2 * | 6/2024 | Shah | A61K 31/47 |
| 2005/0049267 A1 | 3/2005 | Suto et al. | |
| 2005/0209247 A1 | 9/2005 | Cai et al. | |

(Continued)

FOREIGN PATENT DOCUMENTS

| | | |
|---|---|---|
| WO | 2005030140 | 4/2005 |
| WO | 2009136663 | 11/2009 |

(Continued)

OTHER PUBLICATIONS

Kurzrock R et al. "379 Poster A phase I study of XL 184, a MET, VEGFR2, and RET kinase inhibitor, administered orally to patients (pts) with advanced malignancies, including a subgroup of pts with medullary thyroid cancer (MTC)." Eropean journal of cancer. supplement, vol. 6, No. 12, Oct. 1, 2008, 119.

European Medicines Agency, "Specifications: Test procedures and acceptance criteria for new drug substances and new drug products: chemical substances", May 2000.

(Continued)

*Primary Examiner* — D Margaret M Seaman

(74) *Attorney, Agent, or Firm* — Honigman LLP; Heidi M. Berven; Li Gao

(57) ABSTRACT

The present invention is directed to processes for making and compositions containing quinolines such as formula I or pharmaceutically acceptable salts thereof wherein: X1 is H, Br, CI, or X2 is H, Br, CI, or n1 is 1-2; and n2 is 1-2.

22 Claims, No Drawings

(56) References Cited

U.S. PATENT DOCUMENTS

| | | |
|---|---|---|
| 2007/0054928 A1 | 3/2007 | Bannen et al. |
| 2007/0078159 A1 | 4/2007 | Matsushima et al. |
| 2008/0004273 A1 | 1/2008 | Raeppel et al. |
| 2008/0161305 A1 | 7/2008 | Forsyth et al. |
| 2009/0203729 A1 | 8/2009 | Inoue et al. |
| 2009/0274693 A1 | 11/2009 | Gilmer et al. |
| 2011/0059081 A1 | 3/2011 | Bacus |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Kallender et al. |
| 2013/0330377 A1 | 12/2013 | Wilson |
| 2013/0337015 A1 | 12/2013 | Wilson |
| 2014/0057908 A1 | 2/2014 | Smith |
| 2014/0057943 A1 | 2/2014 | Smith |
| 2014/0066444 A1 | 3/2014 | Smith et al. |
| 2014/0121239 A1 | 5/2014 | Aftab et al. |
| 2014/0155396 A1 | 6/2014 | Bannen et al. |
| 2014/0179736 A1 | 6/2014 | Schwab et al. |
| 2014/0200242 A1 | 7/2014 | Wilson |
| 2014/0221372 A1 | 8/2014 | Kulkarni et al. |
| 2014/0228401 A1 | 8/2014 | Aftab et al. |
| 2014/0256938 A1 | 9/2014 | Wison et al. |
| 2014/0302012 A1 | 10/2014 | DeCillis et al. |
| 2014/0323522 A1 | 10/2014 | Aftab et al. |
| 2015/0057310 A1 | 2/2015 | Brown et al. |
| 2015/0133494 A1 | 5/2015 | Aftab et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0031818 A1 | 2/2016 | Aftab et al. |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0057921 A1 | 3/2017 | Wilson et al. |
| 2017/0087143 A1 | 3/2017 | Aftab et al. |
| 2017/0143689 A1 | 5/2017 | Wilson et al. |
| 2017/0266178 A1 | 9/2017 | Wilson et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |
| 2018/0311229 A1 | 11/2018 | Wilson et al. |
| 2019/0030021 A1 | 1/2019 | Wilson et al. |
| 2019/0091215 A1 | 3/2019 | Aftab et al. |
| 2019/0151302 A1 | 5/2019 | Aftab et al. |

FOREIGN PATENT DOCUMENTS

| | | |
|---|---|---|
| WO | 2010083414 | 7/2010 |
| WO | 2010113183 | 10/2010 |
| WO | 2011017639 | 2/2011 |
| WO | 2012009722 | 1/2012 |
| WO | 2012109510 | 6/2012 |

OTHER PUBLICATIONS

Sigma-Aldrich Corporation, "Cabozantinib Material Safety Data Sheet", Version 5.0, Oct. 20, 2014, retrieved from the internet at http://www.sigmaaldrich.com/MSDS/MSDS/DisplayMSDSPage.do?country=US&language=en&productNumber=CDS009101&brand=ALDRICH&PageToGoToURL=http%3A%2F%2Fwww.sigmaaldrich.com%2Fcatalog%2Fproduct%2Faldrich%2Fcds009101%3Flang%3Den on Oct. 1, 2015.

United States Department of Health and Human Services, "Guidance for Industry Q1A(R2) Stability Testing of New Drug Substances and Products", Revision 2, Nov. 2003, retrieved from the internet at www.fda.gov/downloads/drugs/guidancecomplianceregulatory information/guidances/ucm073369.pdf on Oct. 1, 2015.

International Search Report for PCT/US2012/024591, mailed May 25, 2012.

Kibbe, A.H. Handbook of Pharmaceutical Excipients, 3rd edition: American Pharmactical Association and Pharmaceutical Press, ISBN 0-85369-381-1, 2000 (pp. 110,244,305,143,102,501,534,386,160).

Li, Lubricants, 2014, vol. 2, pp. 1-43. (Year: 2014).

"Overview of PHarmaceutical Excipients Used in Tablets and Capsules", 2008, Drug Topics, https://www.drugtopics.com/view/overview-pharmaceutical-excipients-used-tablets-and-capsules. (Year: 2008).

Pingali, Int J Pharm, 2011, vol. 409(0), 269-277. (Year: 2011).

United States Department of Health and Human Services, "Guidance for Industry Q1A(R2) Stability Testing of New Drug Substances and Products", Revision 2, Nov. 2003, retrieved from the internet at https://www.fda.gov/media/71707/download on Jan. 19, 2022.

United States Department of Health and Human Services, "Guidance for Industry Q3B(R2) Impurities in New Drug Products", Revision 2, Aug. 2006, retrieved from the internet at https://www.fda.gov/media/71733/download on Jan. 19, 2022.

Zhang, Y., et al., "XL-184, a MET, VEGFR-2 and RET kinase inhibitor for the treatment of thyroid cancer, clioblastoma multiforme and NSCLC", Idrugs, vol. 13, No. 2, pp. 112-121, Feb. 2010.

Willhauck, M. J., "Neue Therapieoptionen bei fortgeschrittenen Schilddrusenkarzinomen" Deutsche Medizinische Wochenschrift 2011, 136, 1165-1168.

NCT00704288, Study of XL184 in Adults with Glioblastoma Multiformel, view Apr. 7, 2010, ClinicalTrials.gov. https://clinicaltrials.gov/ct2/history/NCT00704288?A=10&B-10.

NCT00704730, Efficacy Study of XL184 in Adults with Medullary Thyroid Cancer, view May 28, 2010, ClinicalTrials.gov. https://clinicaltrials.gov/ct2/history/NCT00704730?A=57&B=57.

Mologni, L., "Development of RET Kinase Inhibitors for Targeted Cancer Therapy" Current Medicinal Chemistry 2011,18, 162-175.

Kurzrock, R., et al., "Activity of XL184 (Cabozantinib), an oral tyrosine kinase inhibitor, in patients with medullary thyroid cancer", Journal of Clinical Oncology, vol. 29, No. 19, pp. 2660-2666, Jul. 1, 2011. Retrieved from the Internet: URL:https://www.ncbi.nlm.nih.gov/pmc/articles/PMC3646303/.

Arko, et al., "Experimental approaches for the treatment of malignant gliomas" Pharmacology & Therapeutics 2010, 128, 1-36.

Handbook of Pharmaceutical Excipients Pharmaceutical Press, 2006 pp. 137, 188, 211, 701, 737 and 738.

Commission Decision dated Feb. 6, 2009.

Michael Aulton e Kevin Taylor, Pharmaceutics: The Science of Dosage Form Design, 2nd Edition, pp. 1 to 679 (Publication Year: 2001).

Rowe, Raymond C., et al., Handbook of Pharmaceutical Excipients, 6th Edition, Pharmaceutical Press and American Pharmacists Association, ISBN 9781582121352 (USA) (Publication Year: 2009).

Ravi Salgia et al., "A phase 1 dose-escalation study of the safety and pharmacokinetics (PK) of XL184, a VEGFR and MET kinase inhibitor, administered orally to patients (pts) with advanced malignancies", Mol Cancer Ther (2007) 6 (11_Supplement): A152 (Publication Date: Nov. 1, 2007).

Berge et al., "Pharmaceutical salts," J Pharm. Sci., 66 (1): 1-19 (Jan. 1977).

Vippagunta, et al., "Crystalline solids", Advanced Drug Delivery Reviews, vol. 48, pp. 3-26, 2001.

Bighley, Lyle D., et al., Salt Forms of Drugs and Absorption, in 13 Encyclopedia of Pharmaceutical Technology 453 (James Swarbrick & James C. Boylan eds., 1995).

Herbert A. Lieberman et al., Pharmaceutical Dosage Forms: Tablets, vol. 1 (2d. Ed., 1989) (PTX-553) Chap. 2-3.

(56) References Cited

OTHER PUBLICATIONS

Esa Landenpaa et al., Crushing Strength, Disintegration Time and Weight Variation of Tablets Compressed from Three Avicel® PH Grades and Their Mixtures, 43 Euro. J. Pharmaceutics and Biopharmaceutics 315 (1997) (DTX-355).

Mira Jivraj et al., An Overview of the Different Excipients Useful for the Direct Compression of Tablets, 3 PSTT 58 (2000) (DTX-344).

Tong et al., In situ Salt Screening—A Useful Technique for Discovery Support and Preformulation Studies, Phann. Dev. Technol. 3 (2), 215-223 (1998) (DTX-243).

FDA, Guideline for Submitting Supporting Documentation in Drug Applications for the Manufacture of Drug Substances, Center for Drug Evaluation and Research (Feb. 1987) (DTX-170).

FDA Guidance for Industry, Genotoxic and Carcinogenic Impurities in Drug Substances and Products: Recommend Approaches (DTX-091).

Complaint for patent infringement—*Exelixis, Inc. v. MSN Laboratories Private Limited et al.*, 1_22-cv-00228, No. 1 (D.Del. Feb. 23, 2022).

Complaint for Patent Infringement—*Exelixis, Inc. v. MSN Laboratories Private Limited et al.*, 1_22-cv-00945, No. 1 (D.Del. Jul. 18, 2022).

Answer to 1 Complaint—*Exelixis, Inc. v. MSN Laboratories Private Limited et al.*, 1_22-cv-00228, No. 9 (D.Del. Feb. 25, 2022).

Answer to 9 Answer to Complaint—*Exelixis, Inc. v. MSN Laboratories Private Limited et al.*, 1_22-cv-00228, No. 15 (D.Del. Mar. 18, 2022).

Answer to Counterclaims—*Exelixis, Inc. v. MSN Laboratories Private Limited et al.*, 1_22-cv-00228, No. 41 (D.Del. Aug. 30, 2022).

Answer to 37 Amended Answer to Complaint—*Exelixis, Inc. v. MSN Laboratories Private Limited et al.*, 1_22-cv-00228, No. 46 (D.Del. Sep. 15, 2022).

Opening Post-Trial Brief on Invalidity—*Exelixis, Inc. v. MSN Laboratories Private Limited et al.*, 1_22-cv-00228, No. 169 (D.Del. Dec. 12, 2023).

Responsive Post-Trial Brief on Noninfringement—*Exelixis, Inc. v. MSN Laboratories Private Limited et al.*, 1_22-cv-00228, No. 173 (D.Del. Jan. 23, 2024).

Answer to 1 Complaint—*Exelixis, Inc. v. MSN Laboratories Private Limited et al.*, 1_22-cv-00945, No. 9 (D.Del. Aug. 9, 2022).

\* cited by examiner

PROCESSES FOR PREPARING QUINOLINE COMPOUNDS AND PHARMACEUTICAL COMPOSITIONS CONTAINING SUCH COMPOUNDS

CROSS-REFERENCE TO RELATED APPLICATIONS

This application is a continuation application of U.S. Ser. No. 18/462,739, filed Sep. 7, 2023, which is a continuation application of U.S. Ser. No. 17/679,634, filed Feb. 24, 2022, which is a continuation application of U.S. Ser. No. 17/170,275, filed Feb. 8, 2021, now U.S. Pat. No. 11,298,349, which is a continuation application of U.S. Ser. No. 17/152,394, filed Jan. 19, 2021, which is a continuation of U.S. application Ser. No. 16/706,323, filed Dec. 6, 2019, which is a division of U.S. application Ser. No. 16/151,653, filed Oct. 4, 2018, now U.S. Pat. No. 10,543,206, which is a division of U.S. application Ser. No. 15/348,716, filed Nov. 10, 2016, now U.S. Pat. No. 10,123,999, which is a division of U.S. application Ser. No. 13/984,559, filed Mar. 20, 2014, now U.S. Pat. No. 9,717,720, which claims priority under 35 U.S.C. § 371 to Patent Cooperation Treaty Application Number PCT/US2012/024591, filed Feb. 10, 2012, which claims the benefit of U.S. Provisional Application No. 61/441,520, filed Feb. 10, 2011, and U.S. Provisional Application No. 61/441,527, filed Feb. 10, 2011, the entire contents of which are incorporated herein by reference.

FIELD OF THE INVENTION

This disclosure relates to processes for preparing compounds useful for modulating protein kinase enzymatic activity. More specifically, this disclosure relates to processes for preparing quinolines that are useful for modulating cellular activities such as proliferation, differentiation, programmed cell death, migration, and chemo-invasion and to pharmaceutical compositions containing such compounds.

BACKGROUND OF THE INVENTION

Traditionally, dramatic improvements in the treatment of cancer are associated with identification of therapeutic agents acting through novel mechanisms. One mechanism that can be exploited in cancer treatment is the modulation of protein kinase activity because signal transduction through protein kinase activation is responsible for many of the characteristics of tumor cells. Protein kinase signal transduction is of particular relevance in, for example, renal, gastric, head and neck, lung, breast, prostate, and colorectal cancers; hepatocellular carcinoma; as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases c-Met, KDR, c-Kit, AxI, flt-3, and flt-4.

The kinase c-Met is the prototypic member of a subfamily of heterodimeric receptor tyrosine kinases (RTKs) which include Met, Ron, and Sea. The endogenous ligand for c-Met is the hepatocyte growth factor (HGF), a potent inducer of angiogenesis. Binding of HGF to c-Met induces activation of the receptor via autophosphorylation, resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59). c-Met overexpression has been demonstrated on a wide variety of tumor types including breast, colon, renal, lung, squamous cell myeloid leukemia, hemangiomas, melanomas, astrocytomas, and glioblastomas. Additionally, activating mutations in the kinase domain of c-Met have been identified in hereditary and sporadic renal papilloma and squamous cell carcinoma. (See, e.g., Maulik et al., Cytokine & growth Factor reviews 2002 13, 41-59; Longati et al., Curr Drug Targets 2001, 2, 41-55; Funakoshi et al., Clinica Chimica Acta 2003 1-23).

Inhibition of epidermal growth factor (EGF), vascular endothelial growth factor (VEGF), and ephrin signal transduction will prevent cell proliferation and angiogenesis, two key cellular processes needed for tumor growth and survival (Matter A., Drug Disc. Technol. 2001 6, 1005-1024). Kinase KDR (refers to kinase insert domain receptor tyrosine kinase) and flt-4 (fins-like tyrosine kinase-4) are both VEGF receptors. Inhibition of EGF, VEGF, and ephrin signal transduction will prevent cell proliferation and angiogenesis, two key cellular processes needed for tumor growth and survival (Matter A. Drug Disc. Technol. 2001 6, 1005-1024). EGF and VEGF receptors are desirable targets for small molecule inhibition. All members of the VEGF family stimulate cellular responses by binding to tyrosine kinase receptors (the VEGFRs) on the cell surface, causing them to dimerize and become activated through transphosphorylation. The VEGF receptors have an extracellular portion with immunoglobulin-like domains, a single transmembrane spanning region, and an intracellular portion containing a split tyrosine-kinase domain. VEGF binds to VEGFR-1 and VEGFR-2. VEGFR-2 is known to mediate almost all of the known cellular responses to VEGF.

Kinase c-Kit (also called stem cell factor receptor or steel factor receptor) is a type 3 receptor tyrosine kinase (RTK) belonging to the platelet-derived growth factor receptor subfamily. Overexpression of c-Kit and c-Kit ligand has been described in variety of human diseases, including human gastrointestinal stromal tumors, mastocytosis, germ cell tumors, acute myeloid leukemia (AML), NK lymphoma, small-cell lung cancer, neuroblastomas, gynecological tumors, and colon carcinoma. Moreover, elevated expression of c-Kit may also relate to the development of neoplasia associated with neurofibromatosis type 1 (NF-1), mesenchymal tumors GISTs, and mast cell disease, as well as other disorders associated with activated c-Kit.

Kinase Flt-3 (fins-like tyrosine kinase-3) is constitutively activated via mutation, either in the juxtamembrane region or in the activation loop of the kinase domain, in a large proportion of patients with AML (Reilly, Leuk. Lymphoma, 2003, 44: 1-7).

Small-molecule compounds that specifically inhibit, regulate, and/or modulate the signal transduction of kinases, such as c-Met, VEGFR2, KDR, c-Kit, Axl, flt-3, and flt-4 described above, are particularly desirable as a means to treat or prevent disease states associated with abnormal cell proliferation and angiogenesis. One such small-molecule is compound IA, which has the chemical structure:

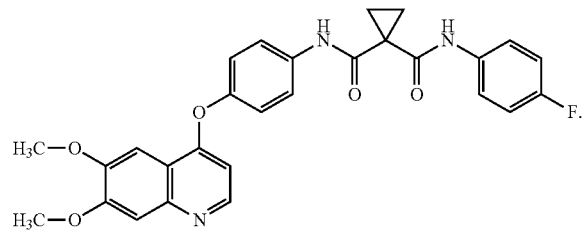

WO2005/030140 describes the synthesis of compound IA (Table 2, Compound 12, Example 48) and also discloses the therapeutic activity of this molecule to inhibit, regulate, and/or modulate the signal transduction of kinases (Assays, Table 4, entry 289), the entire contents of which is incorporated herein by reference.

Although therapeutic efficacy is the primary concern for a therapeutic agent, the pharmaceutical composition can be equally important to its development. Generally, the drug developer endeavors to discover a pharmaceutical composition that possesses desirable properties, such as satisfactory water-solubility (including rate of dissolution), storage stability, hygroscopicity, and reproducibility, all of which can impact the processability, manufacture, and/or bioavailability of the drug.

Accordingly, there is a need for the discovery of new processes for making quinolines such as compound IA that minimize the formation of undesirable process contaminants or byproducts. There is also a need for new pharmaceutical compositions containing quinolines such as compound IA that are essentially free of process byproducts.

SUMMARY OF THE INVENTION

These and other needs are met by the present disclosure, which is directed to processes for making and compositions containing quinolines or pharmaceutically acceptable salts thereof.

In one aspect, the disclosure relates to processes for preparing a compound of formula I:

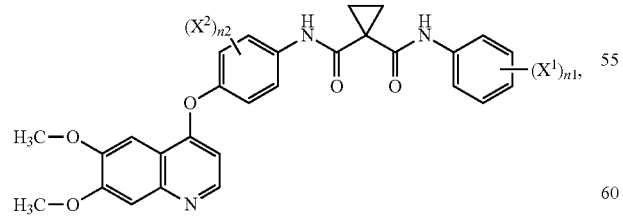

or a pharmaceutically acceptable salt thereof, wherein:
X$^1$ is H, Br, Cl, or F;
X$^2$ is H, Br, Cl, or F;
n1 is 1-2; and
n2 is 1-2.

Intermediates useful in preparing the above compounds are also disclosed.

The compounds of formula I are useful as protein kinase modulators, and they inhibit various protein kinases including Ret and c-Met.

In another aspect, the disclosure provides a process for preparing compound IB:

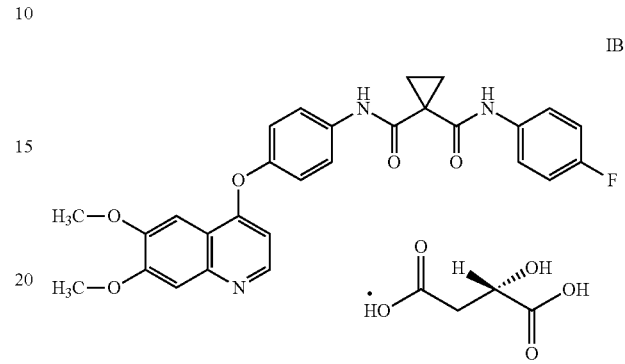

from compound IA:

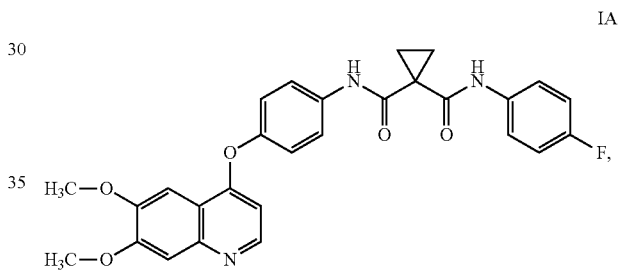

comprising:
(a) heating and agitating a mixture comprising compound IA and L-malic acid, methylethyl ketone, and water;
(b) cooling the mixture;
(c) vacuum distilling the mixture successively; and
(d) isolating the compound of IB by filtration.

In another aspect, the disclosure provides a process for preparing compound IB:

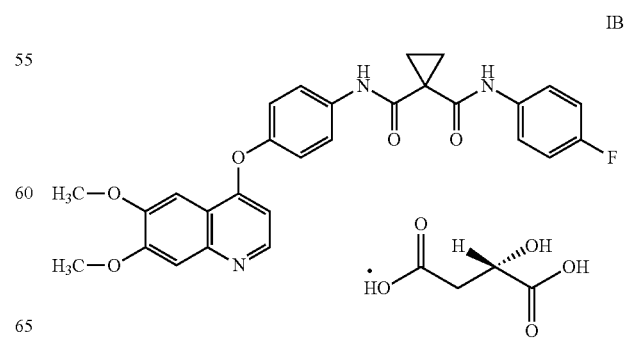

from compound IA:

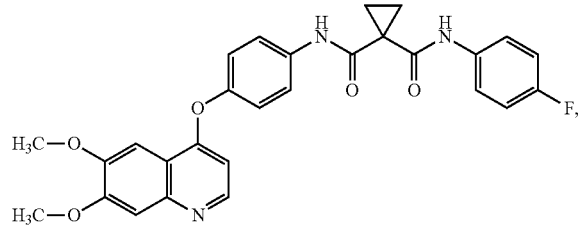

comprising:
(a) heating and agitating a mixture comprising compound IA and L-malic acid, methylethyl ketone, and water;
(b) cooling the mixture;
(c) seeding the mixture with compound IB;
(d) vacuum distilling the mixture; and
(e) isolating compound IB by filtration.

In another aspect, the disclosure provides compound I, IA, or IB admixed with less than 100 ppm 6,7-dimethoxyquinoline-4-ol, the structure of which is

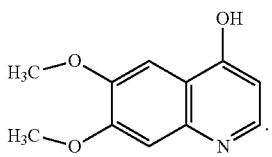

In another aspect, the disclosure provides pharmaceutical compositions containing the compound of formula I, compound IA, or compound IB for oral administration.

In another aspect, the disclosure provides a pharmaceutical tablet composition according to Table 1.

TABLE 1

| Ingredient | % w/w |
|---|---|
| Compound I | 31.68 |
| Microcrystalline Cellulose (MCC) (Avicel PH102) | 38.85 |
| Lactose anhydrous 60M | 19.42 |
| Hydroxypropyl Cellulose, EXF | 3.00 |
| Croscarmellose Sodium | 3.00 |
| Total Intra-granular | 95.95 |
| Silicon dioxide, Colloidal PWD | 0.30 |
| Croscarmellose Sodium | 3.00 |
| Magnesium Stearate | 0.75 |
| Total | 100.00 |

In another aspect, the disclosure provides a pharmaceutical tablet composition according to Table 2.

TABLE 2

| Ingredient | (% w/w) |
|---|---|
| Compound I | 25.0-33.3 |
| Microcrystalline Cellulose, NF | q.s |
| Hydroxypropyl Cellulose, NF | 3 |
| Poloxamer, NF | 0-3 |
| Croscarmellose Sodium, NF | 6.0 |
| Colloidal Silicon Dioxide, NF | 0.5 |
| Magnesium Stearate, NF | 0.5-1.0 |
| Total | 100 |

In another aspect, the disclosure provides a pharmaceutical tablet composition according to Table 2A.

TABLE 2A

| Ingredient | % w/w |
|---|---|
| Compound IB (10% drug load as Compound IA) | 12.67 |
| MCC | 51.52 |
| Lactose | 25.76 |
| Hydroxypropyl cellulose | 3.0 |
| Croscarmellose Sodium | 6.0 |
| Colloidal Silicon Dioxide | 0.3 |
| Magnesium Stearate | 0.75 |
| Total | 100 |

In another aspect, the disclosure provides a pharmaceutical capsule composition according to Table 3.

TABLE 3

| Ingredient | mg/unit dose |
|---|---|
| Compound IB (10% drug load as Compound IA) | 25 |
| Silicified Microcrystalline Cellulose | 196.75 |
| Croscarmellose sodium | 12.5 |
| Sodium starch glycolate | 12.5 |
| Fumed Silica | 0.75 |
| Stearic acid | 2.5 |
| Total Fill Weight | 250 |

In another aspect, the disclosure provides a pharmaceutical capsule composition according to Table 4.

TABLE 4

| Ingredient | mg/unit dose |
|---|---|
| Compound IB (50% drug load as Compound IA) | 100 |
| Silicified Microcrystalline Cellulose | 75.40 |
| Croscarmellose sodium | 10.00 |
| Sodium Starch Glycolate | 10.00 |
| Fumed silica | 0.6 |
| Stearic Acid | 4.0 |
| Total Fill Weight | 200 |

In another aspect, the disclosure provides a pharmaceutical capsule composition according to Table 5, wherein the IB weight equivalents are provided.

TABLE 5

| Ingredient | mg/unit dose 50 mg |
|---|---|
| Compound IB | 63.35 |
| Microcrystalline Cellulose | 95.39 |

TABLE 5-continued

| Ingredient | mg/unit dose 50 mg |
|---|---|
| Croscarmellose sodium | 9.05 |
| Sodium starch glycolate | 9.05 |
| Fumed Silica | 0.54 |
| Stearic acid | 3.62 |
| Total Fill Weight | 181.00 |

In another aspect, the disclosure provides a pharmaceutical capsule composition according to Table 6, wherein the IB weight equivalents are provided.

TABLE 6

| Ingredient | mg/unit dose 60 mg |
|---|---|
| Compound IB | 73.95 |
| Microcrystalline Cellulose | 114.36 |
| Croscarmellose sodium | 10.85 |
| Sodium starch glycolate | 10.85 |
| Fumed Silica | 0.65 |
| Stearic acid | 4.34 |
| Total Fill Weight | 217.00 |

In another aspect, the invention is directed to a pharmaceutical composition comprising compound I, IA, or IB admixed with less than 100 ppm 6,7-dimethoxy-quinoline-4-ol, the structure of which is

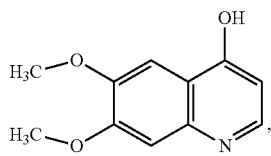

and a pharmaceutically acceptable carrier.

There are many different aspects and embodiments of the disclosure described herein, and each aspect and each embodiment is non-limiting in regard to the scope of the disclosure. The terms "aspects" and "embodiments" are meant to be non-limiting regardless of where the terms "aspect" or "embodiment" appears in this specification. The transitional term "comprising," as used herein, which is synonymous with "including," "containing," or "characterized by," is inclusive or open-ended and does not exclude additional, unrecited elements.

DETAILED DESCRIPTION OF THE INVENTION

Definitions

As used herein, the following words and phrases are generally intended to have the meanings as set forth below, except to the extent that the context in which they are used indicates otherwise or they are expressly defined to mean something different.

The word "can" is used in a non-limiting sense and in contradistinction to the word "must." Thus, for example, in many aspects of the invention a certain element is described as "can" having a specified identity, which is meant to convey that the subject element is permitted to have that identity according to the invention but is not required to have it.

If a group "R" is depicted as "floating" on a ring system, then unless otherwise defined, the substituent(s) "R" can reside on any atom of the ring system, assuming replacement of a depicted, implied, or expressly defined hydrogen from one of the ring atoms, so long as a stable structure is formed.

When there are more than one such depicted "floating" groups, such as where there are two groups; then, unless otherwise defined, the "floating" groups can reside on any atoms of the ring system, again assuming each replaces a depicted, implied, or expressly defined hydrogen on the ring.

"Pharmaceutically acceptable salts" include acid addition salts.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, or mixtures thereof, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, or mixtures thereof.

"Essentially free" as used in the phrase "essentially free of process byproducts or contaminants," means that a compound or composition as disclosed here in is admixed with 200 parts per million (ppm) or less of such byproducts or contaminants.

The disclosure is further illustrated by the following examples, which are not to be construed as limiting the disclosure in scope or spirit to the specific procedures described in them. Unless specified otherwise, the starting materials and various intermediates may be obtained from commercial sources, prepared from commercially available organic compounds, or prepared using well-known synthetic processes.

Processes

Aspect 1: Processes for Making Compounds of Formula I

Aspect (1) of the invention relates to a process of preparing a compound of formula I:

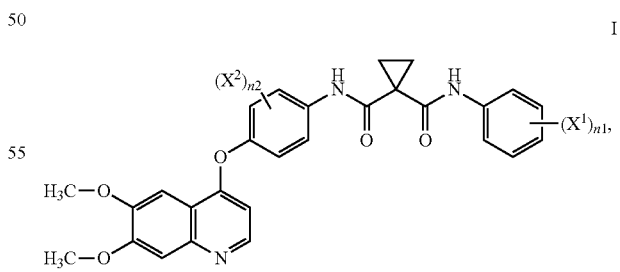

or a pharmaceutically acceptable salt thereof, wherein:

$X^1$ is H, Br, Cl, or F;

$X^2$ is H, Br, Cl, or F;

n1 is 1-2; and n2 is 1-2;

the process comprising:
  contacting the compound of formula g(1) with reactant z(1) to yield the compound of formula I:

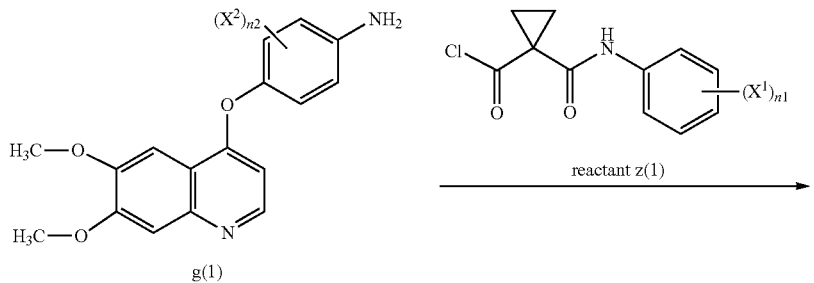

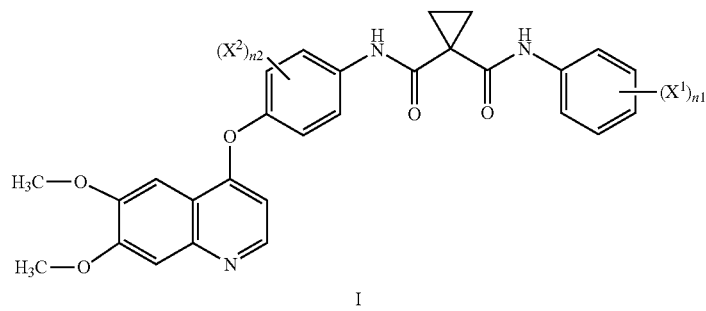

The reaction is advantageously carried out under suitable reaction conditions. Non-limiting examples of suitable reaction conditions include using basic conditions. Non-limiting examples of basic conditions that can be used in Aspect (1) include the use of inorganic bases, such as aqueous KOH, NaOH, $K_2CO_3$, $Na_2CO_3$, $K_3PO_4$, $Na_3PO_4$, $K_2HPO_4$, $Na_2HPO_4$, and the like, or mixtures thereof. Other non-limiting examples of suitable reaction conditions include using suitable solvents. Non-limiting examples of suitable solvents that can be used include water miscible solvents, such as THF, acetone, ethanol, and the like, or mixtures thereof. Other non-limiting examples of suitable reaction conditions include using suitable temperatures. Suitable temperatures that may be used for the reaction include a temperature at a range from about 10° C. to about 30° C., or alternatively, at a range from about 15° C. to about 28° C., or alternatively, at a range from about 20° C. to about 25° C. The product formed by the reaction is in the free base form, and this free base form may be converted into a pharmaceutically acceptable salt thereof by processes known in the art. For example, the compound of formula I can be converted to the L-malate salt by the addition of L-malic acid and a suitable solvent.

Utilities of the compound of formula I are further described in WO 2005/030140 A2, which is incorporated herein by reference.

Embodiments of Aspect (1) Part A

In another embodiment of Aspect (1), $X^1$ is Cl or F.
In another embodiment of Aspect (1), $X^2$ is Cl or F.
In another embodiment of Aspect (1), $X^1$ is F.
In another embodiment of Aspect (1), $X^2$ is F.
In another embodiment of Aspect (1), $X^1$ is H.
In another embodiment of Aspect (1), $X^2$ is H.
In another embodiment of Aspect (1), n1 is 1.
In another embodiment of Aspect (1), n2 is 1.
In another embodiment of Aspect (1), n1 is 2.
In another embodiment of Aspect (1), n2 is 2.

All compounds of formula I for Aspect (1) disclosed above include any of the disclosed alternative embodiments in Part A for each of $X^1$, $X^2$, n1 or n2, in combination with any other of the disclosed alternative embodiments in Part A for each of $X^1$, $X^2$, n1, or n2, as well as a pharmaceutically acceptable salt of any such combination.

Embodiments of Aspect (1) Part B

In another embodiment of Aspect (1), n1 and n2 are each 1.
In another embodiment of Aspect (1), n1 and n2 are each 2.
In another embodiment of Aspect (1), n1 is 1; and n2 is 2.
In another embodiment of Aspect (1), n1 is 2 and n2 is 1.
In another embodiment of Aspect (1), $X^1$ is H; and $X^2$ is F.
In another embodiment of Aspect (1), $X^1$ is F; and $X^2$ is H.
In another embodiment of Aspect (1), $X^1$ and $X^2$ are each H.
In another embodiment of Aspect (1), $X^1$ and $X^2$ are each F.
In another embodiment of Aspect (1), $X^1$ is Cl; and $X^2$ is H.
In another embodiment of Aspect (1), $X^1$ is H; and $X^2$ is Cl.
In another embodiment of Aspect (1), $X^1$ and $X^2$ are each Cl.
In another embodiment of Aspect (1), $X^1$ is Cl; and $X^2$ is F.
In another embodiment of Aspect (1), $X^1$ is F; and $X^2$ is Cl.

Embodiments of Aspect (1) Part C

In an embodiment of Aspect (1), the compound of formula g(1) can be made by reacting a compound of formula f(1) with reactant y(1) to yield the compound of g(1):

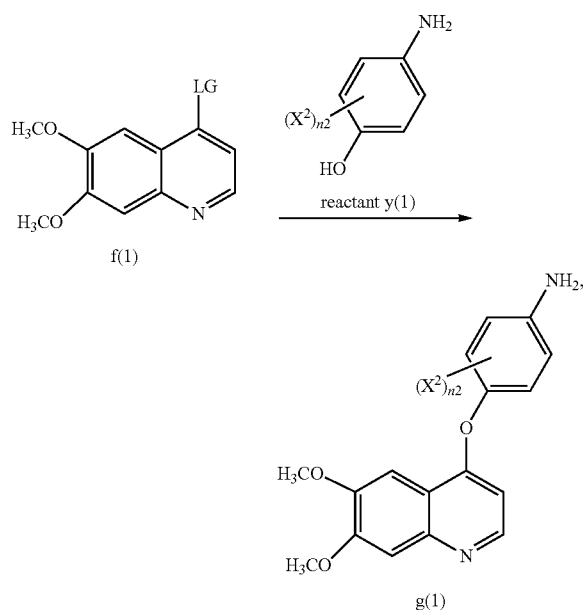

wherein LG represents a leaving group, and each of $X^2$, and n2 are as defined in Aspect (1), or as in any of the embodiments of Aspect (1) Part A. A non-limiting example of a leaving group includes a halo group such as Cl, Br, or F. Various compounds of reactant y(1) are commercially available, such as 2-fluoro-4-aminophenol and 4-aminophenol. Also, the skilled artisan would be able to make any variation of reactant y(1) using commercially available starting materials and by using known techniques to modify these commercially available starting materials to yield various compounds within the scope of reactant y(1).

The reaction in this embodiment is advantageously carried out under suitable reaction conditions. Non-limiting examples of suitable reaction conditions include using suitable solvents such as polar solvents. Non-limiting examples of polar solvents that can be used include tetrahydrofuran (THF), dimethylacetamide (DMA), dimethylsulfoxide (DMSO), dimethylformamide (DMF), ethyl acetate, N-methyl pyrrolidone (NMP), propylene carbonate, and the like, or mixtures thereof. In another embodiment, the polar solvent is dimethylacetamide (DMA). In another embodiment, the polar solvent is dimethylsulfoxide (DMSO). In another embodiment, the polar solvent is dimethylformamide (DMF). In another embodiment, the polar solvent is ethyl acetate. In another embodiment, the polar solvent is N-methyl pyrrolidone (NMP). In another embodiment, the polar solvent is propylene carbonate. In another embodiment, the solvent is a mixture of solvents, such as a mixture comprising THF and DMA.

The reactants f(1) and y(1) can be added together at a temperature ranging from about 10° C. to about 30° C., or alternatively, from about 15° C. to about 28° C., or alternatively, from about 20° C. to about 25° C. The mixture is then heated to a temperature ranging from about 80° C. to about 125° C., or alternatively, from about 95° C. to about 110° C., or alternatively, from about 100° C. to about 105° C., and the selected temperature is maintained until the reaction is complete.

Other non-limiting examples of suitable reaction conditions in this step of Aspect (1) include the use of a suitable base, such as a metal hydroxide or a non-nucleophilic base. Examples of metal hydroxides include sodium hydroxide or potassium hydroxide. Non-limiting examples of non-nucleophilic bases that can be used include lithium diisopropylamide, lithium tetramethylpiperidide, and alkali metal alkoxides such as sodium tert-butoxide, potassium tert-butoxide, sodium-pentoxide, and the like, or mixtures thereof. Preferably, the base is sodium tert-butoxide or sodium tert-pentoxide. In one embodiment, the base is sodium tert-pentoxide. Typically the sodium tert-pentoxide is commercially available as 35 weight percent solution of base in tetrahydrofuran, or as a 95 weight percent solid reagent. Preferably, the sodium tert-pentoxide is a 95 weight percent solid.

Typically, approximately 1.1 to 3.0 molar equivalents of base are used relative the moles of f(1) that are used. More preferably, 1.3 to 2.5 molar equivalents of base are used relative the moles of f(1) that are used. More preferably, 1.5 to 2.2 molar equivalents of base are used relative the moles of f(1) that are used. More preferably, 1.7 to 2.1 molar equivalents of base are used relative the moles of f(1) that are used.

Typically, the amount of molar equivalents of amino phenol that are used exceeds the molar equivalents of base that are used. In one embodiment, 1.1 to 2 molar equivalents of amino phenol are used relative to the molar equivalents of base that are used.

Once the reaction is substantially complete, the reaction mixture can be cooled to a temperature ranging from about 10° C. to about 25° C. Precooled water can be charged at a rate to maintain a temperature that ranges from about 5° C. to about 35° C. Alternatively, the precooled water can be charged at a rate to maintain a temperature that ranges from about 10° C. to about 25° C. As a non-limiting example, the precooled water can be at a temperature ranging from about 0° C. to about 10° C. As another non-limiting example, the precooled water can be at a temperature ranging from about 2° C. to about 7° C. The precipitate can be collected by filtration under standard conditions and purified by standard purification techniques.

Embodiments of Aspect (1) Part D

In an embodiment of Aspect (1), the compound of formula f(1) can be made by converting a compound of formula e(1) to the compound of formula f(1):

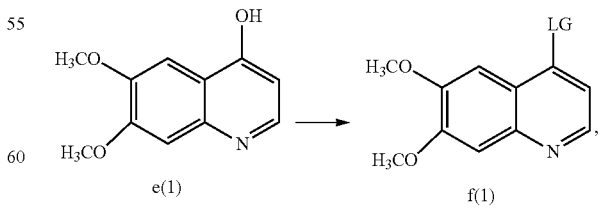

wherein LG represents a leaving group. Non-limiting examples of leaving groups that can be used include halo groups (e.g., Cl, Br, or F) that can be added by halogenating agents. Non-limiting examples of halogenating agents that can be used include chlorinating agents, such as SOCl$_2$, SO$_2$Cl$_2$, COCl$_2$, PCl$_5$, POCl$_3$, and the like.

The reaction is advantageously carried out under suitable reaction conditions. Non-limiting examples of suitable reaction conditions in Part D of Aspect (1) include the use of suitable solvents. Non-limiting example of suitable solvents that can be used during the halogenation of the compound of formula e(1) include a polar, aprotic solvent, such as CH$_3$CN, DMF, and the like, or mixtures thereof. In other embodiments, the chlorination can be carried out using POCl$_3$ in acetonitrile, COCl$_2$ in DMF, or SOCl$_2$ in DMF. The addition of the chlorination agent is advantageously carried out at a temperature ranging from about 60° C. to about 90° C. In another embodiment, the addition of the chlorination agent can be carried out at a temperature ranging from about 70° C. to about 85° C. In another embodiment, the addition of the chlorination agent can be carried out at a temperature ranging from about 74° C. to about 80° C. The product can then be collected by filtration and purified using standard techniques.

Embodiments of Aspect (1) Part E

In an embodiment of Aspect (1), reactant z(1) can be made by reacting reactant z(1a) with a chlorinating agent to yield reactant z(1):

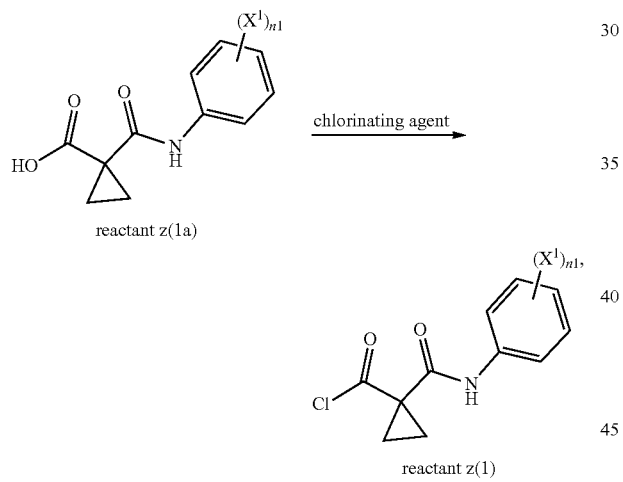

wherein X$^1$ is Br, Cl, or F; and n1 is 1-2. Compounds of reactant z(1a) can be made according to the process described in Example 25 of WO 2005/030140 A2, and the skilled artisan would be able to make any necessary substitutions using commercially available starting materials to come up with various compounds within the scope of reactant z(La). Example 25 in WO 2005/030140 A2 is incorporated herein by reference.

The reaction is advantageously carried out under suitable reaction conditions. Non-limiting examples of suitable reaction conditions include using a chlorinating agent such as POCl$_3$, oxalyl chloride, and the like. In another embodiment, oxalyl chloride is used as a chlorinating agent. Non-limiting examples of suitable reaction conditions include carrying out the reaction at a temperature in the range from about 0° C. to about 25° C., or alternatively at a temperature in the range from about 5° C. to about 20° C. Other non-limiting examples of suitable reaction conditions include carrying out the reaction in a suitable solvent. Non-limiting examples of suitable solvents that can be used include polar aprotic solvents, such as halogenated hydrocarbons (e.g., dichloromethane and chloroform), ethers (e.g., Et$_2$O), dioxane, tetrahydrofuran (THF) containing catalytic DMF, and the like, or mixtures thereof. The resulting solution containing reactant z(1) can be used, without further processing, to make the compound of formula I.

Other Embodiments of Aspect (1)

In another embodiment of Aspect (1), the compound of formula I is a compound of formula IA-1:

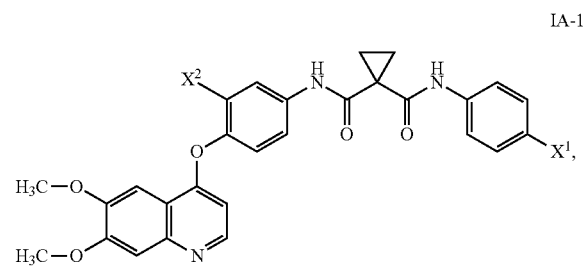

or a pharmaceutically acceptable salt thereof, wherein:
X$^1$ is H, Cl, Br, or F; and X$^2$ is H, Cl, Br, or F. Compound IA can be in the free base form or it can converted to a pharmaceutically acceptable salt thereof. Accordingly, compound IA can be converted to its L-malate salt by the addition of L-malic acid and a suitable solvent.

In another embodiment of Part D of Aspect (1), the compound of formula e(1) is compound e(2):

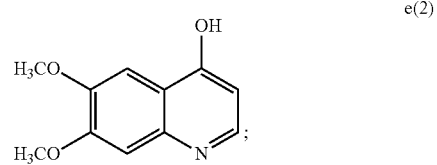 [SMILES: COc1cc2nccc(O)c2cc1OC]

and the compound of formula f(1) is compound f(2):

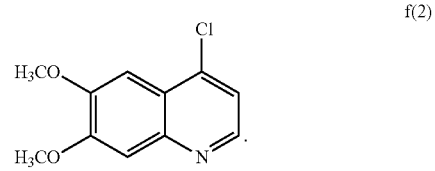

In another embodiment of Part C of Aspect (1), the compound of formula f(1) is compound f(2):

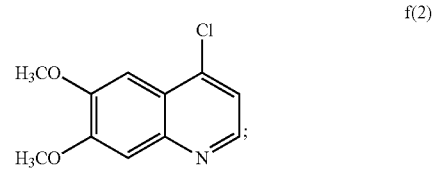 [SMILES: COc1cc2nccc(Cl)c2cc1OC]

reactant y(1) is reactant (y)(2):

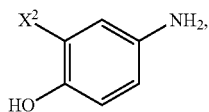

wherein $X^2$ is hydrogen or fluoro; and
the compound of formula g(1) is of formula g(2):

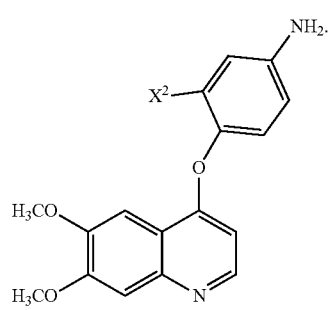

In a further embodiment, the reaction employs a non-nucleophilic base. In a further embodiment, the non-nucelophilic base is an alkali metal alkoxide; and the reaction is carried out in a polar solvent. In a further embodiment, the alkali metal alkoxide is sodium tert-butoxide, and the polar solvent is DMA.

In another embodiment of Part C of Aspect (1), the compound of formula f(1) is

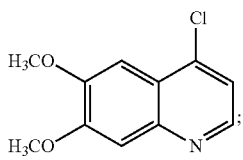

reactant y(1) is reactant (y)(3):

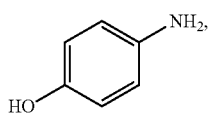

wherein $X^2$ is hydrogen or fluoro; and
the compound of formula g(1) is compound g(3):

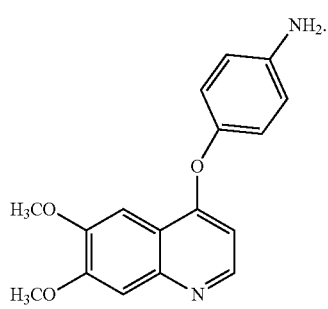

In another embodiment of Aspect (1) of this disclosure, the compound of formula g(1) is compound g(3):

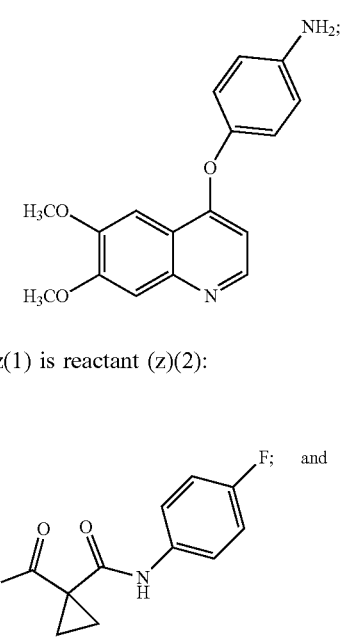

reactant z(1) is reactant (z)(2):

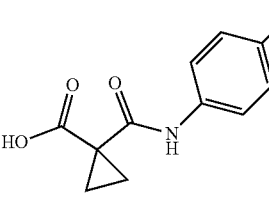

the compound of formula I is compound IA:

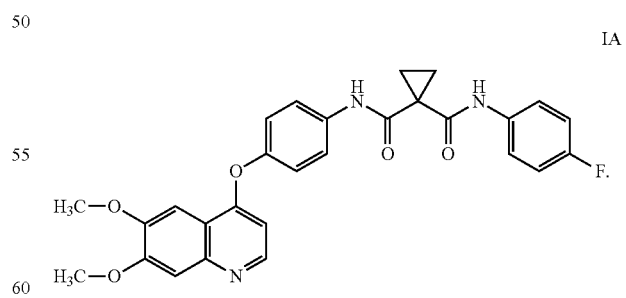

In a further embodiment, the reaction is carried out in the presence of an inorganic base. In a further embodiment, the inorganic base is $K_2CO_3$, and the solvent employed in this reaction is a combination of THF and $H_2O$.

In another embodiment of Aspect (1) of this disclosure, $X^1$ and $X^2$ for each of formula g(1) and reactant z(1) are each selected from Cl or F. In another embodiment, $X^1$ and $X^2$ for each of formula g(2), and reactant z(1) are both F.

The compound of formula f(2), or a pharmaceutically acceptable salt thereof, can be made by converting the compound of formula e(2) to a compound of formula f(2) with a chlorinating agent in a suitable solvent:

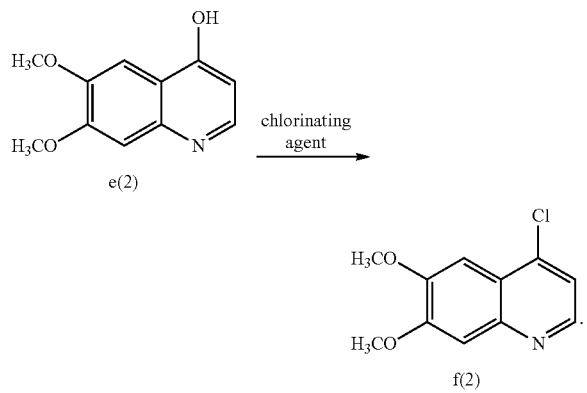

The compound of formula f(2) can be in its free base form or converted to a pharmaceutically acceptable salt thereof. The reaction conditions that can be used in this aspect include any of the reaction conditions disclosed in Part E of Aspect (1).

Aspect 2: Processes for Making Compounds of Formula g(2)

Aspect (2) of the disclosure relates to a process of preparing compound g(2):

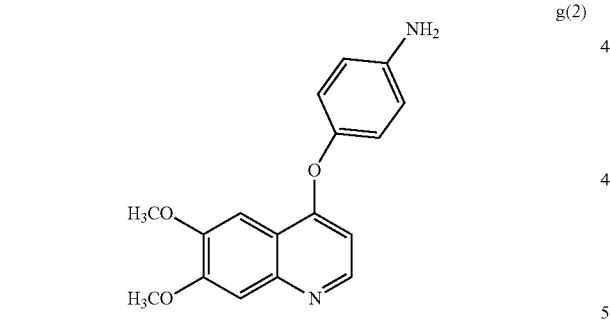

or a pharmaceutically acceptable salt thereof; the process comprising reacting compound f(2) with reactant y(3) under basic conditions (e.g., using 2,6-lutidine) in an appropriate solvent to yield compound g(3):

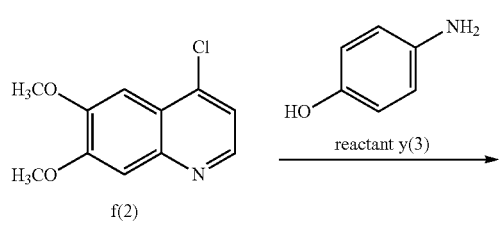

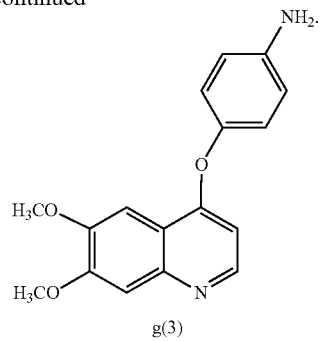

The reaction conditions that can be used in this aspect include any of the reaction conditions disclosed in Part C of Aspect (1).

Alternative reaction conditions that can be used in this aspect include any of the reaction conditions disclosed in Parts C and D of Aspect (1).

Aspect 3: Processes for Making Compounds of IB

As indicated above, in one aspect, the invention provides a process for preparing compound IB:

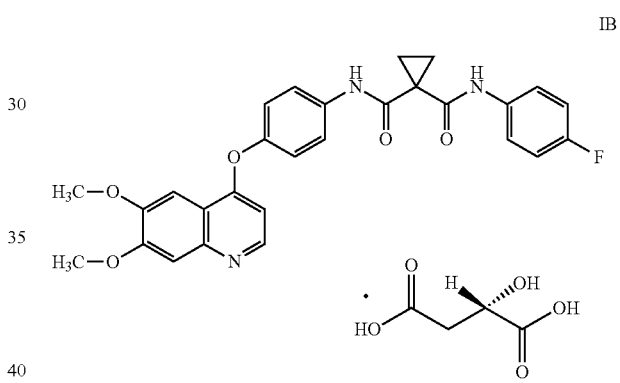

from compound IA:

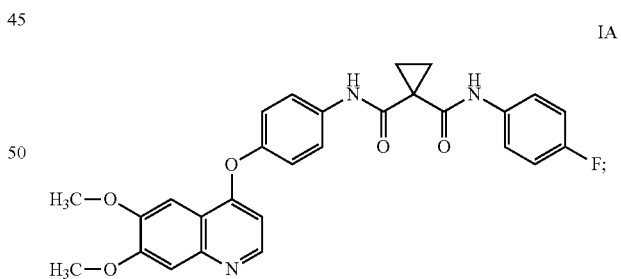

comprising:
(a) heating and agitating a mixture comprising compound IA and L-malic acid, methylethyl ketone, and water;
(b) cooling the mixture;
(c) vacuum distilling the mixture successively; and
(d) isolating the compound of IB by filtration.

In one embodiment of this aspect, compound IA is admixed with a sufficient amount of L-malic acid in a methylethyl ketone (MEK)/water (1:1) mixture. Alternatively, L-malic acid is added as a solution in water to a mixture of compound IA in methyl ethyl ketone. Generally the amount of L-malic is greater than 1 molar equivalent relative to compound IA. The mixture of compound IA and L-malic acid in MEK/water is heated at about 40-70° C., and preferably at about 50-60° C., and more preferably at about 55-60° C. with agitation, such as by stirring or the like, for about 1 to about 5 hours. At the end of the heating, the mixture is optionally clarified by filtering to give a clear solution. The resulting clear solution is then vacuum distilled from 1 to about 5 times at 150 to 200 mm Hg and a maximum jacket temperature of 55° C. to provide the desired crystalline compound of IB.

In one embodiment, L-malic acid is charged as a solution in water to compound IA. Generally the amount of L-malic is greater than 1 molar equivalent relative to compound IA. The mixture of compound IA and L-malic acid in MEK/water is heated at about 40-70° C., and preferably at about 50-60° C., and more preferably at about 55-60° C. with agitation, such as by stirring or the like, for about 1 to about 5 hours. At the end of the heating, the mixture is optionally clarified by filtering to give a clear solution which is at a temperature of about 30-40° C., and more preferably at a temperature of about 33-37° C. This clear solution is optionally seeded to facilitate crystallization. After seeding, the resulting mixture is vacuum distilled as provided above.

In one embodiment, compound IB is in the N-1 form. In another embodiment, compound IB is in the N-2 form. In another embodiment, compound IB is a mixture of the N-1 form and the N-2 form. Processes for preparing the N-1 and N-2 forms of compound IB are disclosed in WO 2010/083414 (PCT/US2010021194), the entire contents of which are incorporated herein by reference.

In another embodiment, the disclosure relates to compound IA or IB admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

In another embodiment, the disclosure relates to compound IA admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

In another embodiment, the disclosure relates to compound IB admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

In another embodiment, the disclosure relates to compound IB in the N-1 form admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

In another embodiment, the disclosure relates to compound IB in the N-2 form admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

In another embodiment, the disclosure relates to compound IB as a mixture of the N-1 form and the N-2 form admixed with 100 ppm or less of 6,7-dimethoxy-quinoline-4-ol. In one embodiment, the compound is admixed with 50 ppm or less of 6,7-dimethoxy-quinoline-4-ol. In another embodiment, the compound is admixed with 25 ppm or less of 6,7-dimethoxy-quinoline-4-ol. In another embodiment, the compound is admixed with 10 ppm or less of 6,7-dimethoxy-quinoline-4-ol. In another embodiment, the compound is admixed with 5 ppm or less of 6,7-dimethoxy-quinoline-4-ol. In another embodiment, the compound is admixed with 2.5 ppm or less of 6,7-dimethoxy-quinoline-4-ol.

Pharmaceutical Compositions

In another embodiment, the disclosure relates to a pharmaceutical composition comprising Compound I, IA, or IB. Various carriers used in formulating pharmaceutically acceptable compositions and known techniques for their bulk preparation and subsequent production into unit dosage forms are employed to make the pharmaceutical compositions disclosed herein and are described in Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York. The amount of carriers and excipients used in a composition can be varied proportionally according to the amount of active ingredient used (that is, Compound I, IA or IB).

In one embodiment, the pharmaceutical composition is a tablet.

In another embodiment, the pharmaceutical composition is a capsule.

In another embodiment, the pharmaceutical composition comprises Compound IA.

In another embodiment, the pharmaceutical composition comprises Compound IB.

In another embodiment, the pharmaceutical composition comprises Compound IB. as the N-1 polymorph.

In another embodiment, the pharmaceutical composition comprises Compound IB as the N-2 polymorph.

In another embodiment, the pharmaceutical composition comprises Compound IB as a mixture of the N-1 form and the N-2 form.

In another embodiment, the disclosure relates to a pharmaceutical composition comprising Compound IA or IB; one or more fillers; one or more disintegrants; one or more glidants; and one or more lubricants.

In this embodiment, the filler comprises microcrystalline cellulose.

In this embodiment, the disintegrant comprises croscarmellose sodium.

In this embodiment, the disintegrant comprises croscarmellose sodium and sodium starch glycolate.

In this embodiment, the glidant comprises fumed silica.

In this embodiment, the lubricant comprises stearic acid.

In another embodiment, the disclosure relates to a pharmaceutical composition comprising Compound IA or IB; microcrystalline cellulose; lactose; hydroxypropyl cellulose; croscarmellose sodium; colloidal silicon dioxide; and magnesium stearate.

In another embodiment, the disclosure relates to a pharmaceutical composition comprising Compound IA or IB; microcrystalline cellulose; hydroxypropyl cellulose; a surfactant; croscarmellose sodium; colloidal silicon dioxide; and magnesium stearate.

In another embodiment, the disclosure relates to a pharmaceutical composition comprising Compound IA or IB; microcrystalline cellulose; croscarmellose sodium; fumed silica; and stearic acid.

In another embodiment, the disclosure relates to a pharmaceutical composition comprising Compound IA or IB; microcrystalline cellulose; anhydrous lactose; hydroxypropyl cellulose; croscarmellose sodium; silicon dioxide; and magnesium stearate.

In another embodiment, the disclosure relates to a pharmaceutical composition comprising Compound IA or IB; microcrystalline cellulose; anhydrous lactose; hydroxypropyl cellulose; a surfactant; croscarmellose sodium; silicon dioxide; and magnesium stearate.

In another aspect, the disclosure provides a pharmaceutical composition according to Tables 1, 2, 2A, 3, 4, 5, and 6 as provided above. The compositions are prepared according to methods available to the skilled artisan. For example, the Tablet formulations are prepared by combining, blending, and compacting the components of the tablet compositions. The capsule compositions are prepared by combining and blending the components and then placing the blend in a gelatin capsule.

For example, the 25 mg capsules (Table 3, 10 percent drug load formulation) are prepared as follows. The drug substance is delumped through a mill. The delumped drug substance is then co-screened with an equal volume Prosolv HD90. The excipients, except for stearic acid, are screened and charged to a blender along with the co-screened drug substance. The mixture is blended in a V-Blender. This process is repeated to manufacture a second sublot of unlubricated blend. The two sublots are then combined together in a V-blender and lubricated with stearic acid which has been co-screened with an equal volume of unlubricated blend. The final blend is then encapsulated into opaque, size 1 gelatin capsules using an automated capsule filling machine. The capsules are then weight sorted through an automatic weight sorter.

The 100-mg capsules (Table 4, 50% drug load formulation) are manufactured in two equal sublots of 5 kg of blend which are combined prior to lubricant blend The drug substance is delumped through a mill. The excipients, except for stearic acid, are screened and charged to the mixer along with the delumped drug substance. The mixture is blended with a high shear mixer. The process is repeated to manufacture a second sublot of unlubricated blend. The final blend is then encapsulated into Swedish oraopaque, size 1 gelatin capsules using an automated capsule filling machine. The capsuare then weight sorted through an automatic weight sorter.

The 50 and 60 mg capsules (Tables 5 and 6) are prepared in a similar fashion as the 25 and 100 mg capsules.

In another aspect, the disclosure relates to a pharmaceutical composition comprising a compound of Formula IA or IB and a pharmaceutically acceptable carrier admixed with less than 100 ppm of 6,7-dimethoxy-quinoline-4-ol. 6,7-dimethoxy-quinoline-4-ol, the structure of which is

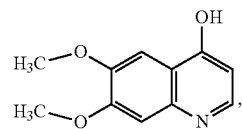

can be used as reagent e(1) to make chloride f(1) and is a byproduct that may form during the synthesis of Compound IA or IB. Minimizing the concentration of contaminants or byproducts such as 6,7-dimethoxy-quinoline-4-ol in pharmaceutical compositions destined for human administration is desirable.

In one embodiment, the pharmaceutical composition as defined in any of the previous embodiments (for example, the pharmaceutical composition of Tables 1, 2, 2A, 3, 4, 5, and 6) is admixed with 100 ppm 6,7-dimethoxy-quinoline-4-ol.

In another embodiment, the pharmaceutical composition as defined in any of the previous embodiments is admixed with 50 ppm 6,7-dimethoxy-quinoline-4-ol.

In another embodiment, the pharmaceutical composition as defined in any of the previous embodiments is admixed with 25 ppm 6,7-dimethoxy-quinoline-4-ol.

In another embodiment, the pharmaceutical composition as defined in any of the previous embodiments is admixed with 15 ppm 6,7-dimethoxy-quinoline-4-ol.

In another embodiment, the pharmaceutical composition as defined in any of the previous embodiments is admixed with 10 ppm 6,7-dimethoxy-quinoline-4-ol.

In another embodiment, the pharmaceutical composition as defined in any of the previous embodiments is admixed with 5 ppm 6,7-dimethoxy-quinoline-4-ol.

In another embodiment, the pharmaceutical composition as defined in any of the previous embodiments is admixed with 2.5 ppm 6,7-dimethoxy-quinoline-4-ol.

In another embodiment, the disclosure relates to a pharmaceutical composition comprising Compound IA or IB; one or more fillers; one or more disintegrants; one or more glidants; and one or more lubricants admixed with 100 ppm or less 6,7-dimethoxy-quinoline-4-ol.

In this embodiment, the filler comprises microcrystalline cellulose.

In this embodiment, the disintegrant comprises croscarmellose sodium.

In this embodiment, the disintegrant comprises croscarmellose sodium and sodium starch glycolate.

In this embodiment, the glidant comprises fumed silica.

In this embodiment, the lubricant comprises stearic acid.

In another embodiment, the disclosure relates to a pharmaceutical composition comprising Compound IA or IB; microcrystalline cellulose; croscarmellose sodium; fumed silica; and stearic acid; admixed with 100 ppm or less of 6,7-dimethoxy-quinoline-4-ol. In one embodiment of this embodiment, the composition is admixed with 50 ppm or less of 6,7-dimethoxy-quinoline-4-ol. In another embodiment of this embodiment, the composition is admixed with 25 ppm or less of 6,7-dimethoxy-quinoline-4-ol. In another embodiment of this embodiment, the composition is admixed with 10 ppm or less of 6,7-dimethoxy-quinoline-4-ol. In another embodiment of this embodiment, the composition is admixed with 5 ppm or less of 6,7-dimethoxy-quinoline-4-ol. In another embodiment of this embodiment, the composition is admixed with 2.5 ppm or less of 6,7-dimethoxy-quinoline-4-ol.

In another embodiment, the disclosure relates to a pharmaceutical composition comprising Compound IA or IB; microcrystalline cellulose; anhydrous lactose; hydroxypropyl cellulose; a surfactant; croscarmellose sodium; silicon dioxide; and magnesium stearate; admixed with 100 ppm or less of 6,7-dimethoxy-quinoline-4-ol. In one embodiment of this embodiment, the composition is admixed with 50 ppm or less of 6,7-dimethoxy-quinoline-4-ol. In another embodiment of this embodiment, the composition is admixed with 25 ppm or less of 6,7-dimethoxy-quinoline-4-ol. In another embodiment of this embodiment, the composition is admixed with 10 ppm or less of 6,7-dimethoxy-quinoline-4-ol. In another embodiment of this embodiment, the composition is admixed with 5 ppm or less of 6,7-dimethoxy-quinoline-4-ol. In another embodiment of this embodiment, the composition is admixed with 2.5 ppm or less of 6,7-dimethoxy-quinoline-4-ol.

In another embodiment, the disclosure relates to a pharmaceutical composition comprising Compound IA or IB; microcrystalline cellulose; croscarmellose sodium; fumed silica; and stearic acid; admixed with 100 ppm or less of 6,7-dimethoxy-quinoline-4-ol. In one embodiment of this embodiment, the composition is admixed with 50 ppm or less of 6,7-dimethoxy-quinoline-4-ol. In another embodiment of this embodiment, the composition is admixed with 25 ppm or less of 6,7-dimethoxy-quinoline-4-ol. In another embodiment of this embodiment, the composition is admixed with 10 ppm or less of 6,7-dimethoxy-quinoline-4-ol. In another embodiment of this embodiment, the composition is admixed with 5 ppm or less of 6,7-dimethoxy-quinoline-4-ol. In another embodiment of this embodiment, the composition is admixed with 2.5 ppm or less of 6,7-dimethoxy-quinoline-4-ol.

EXAMPLES

The invention is illustrated further by the following examples in Scheme 1 and the description thereof, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations. Unless otherwise specified, all reagents and solvents are of standard commercial grade and are used without further purification. The appropriate atmosphere to run the reaction under, for example, air, nitrogen, hydrogen, argon, and the like, will be apparent to those skilled in the art.

Preparation of N-(4-{[6,7-bis(methyloxy)quinolin-4-yl]oxy}phenyl)-N'-(4-fluorophenyl)cyclopropane-1,1-dicarboxamide and the (L)-malate salt thereof A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in FIG. 1:

Figure 1

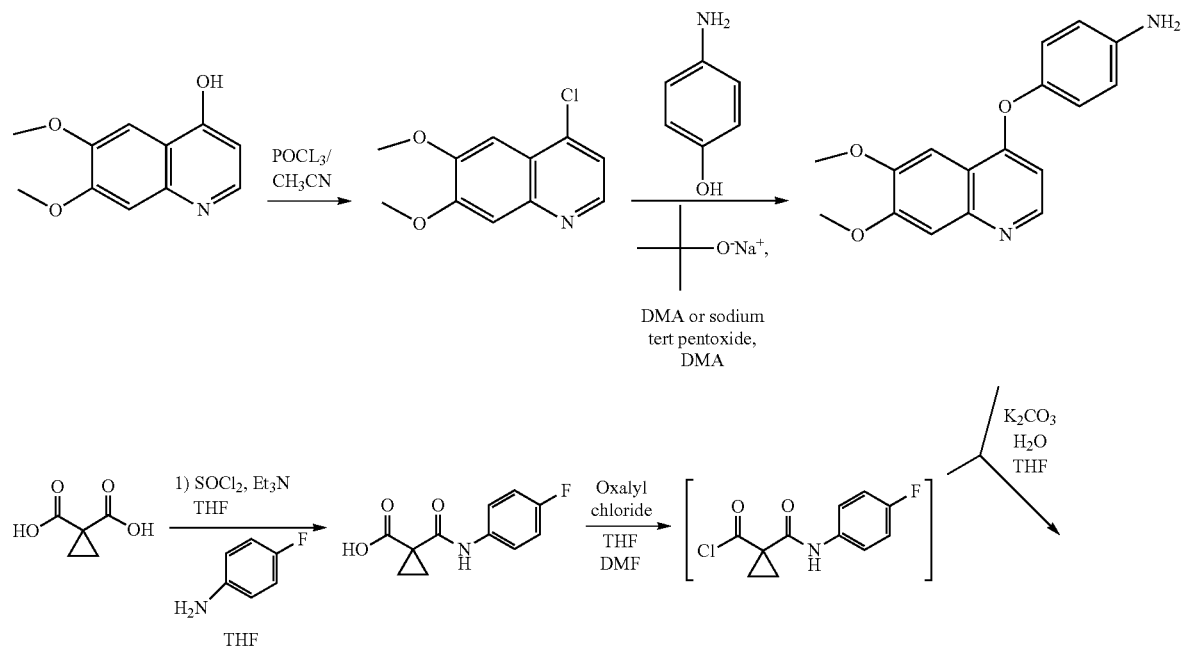

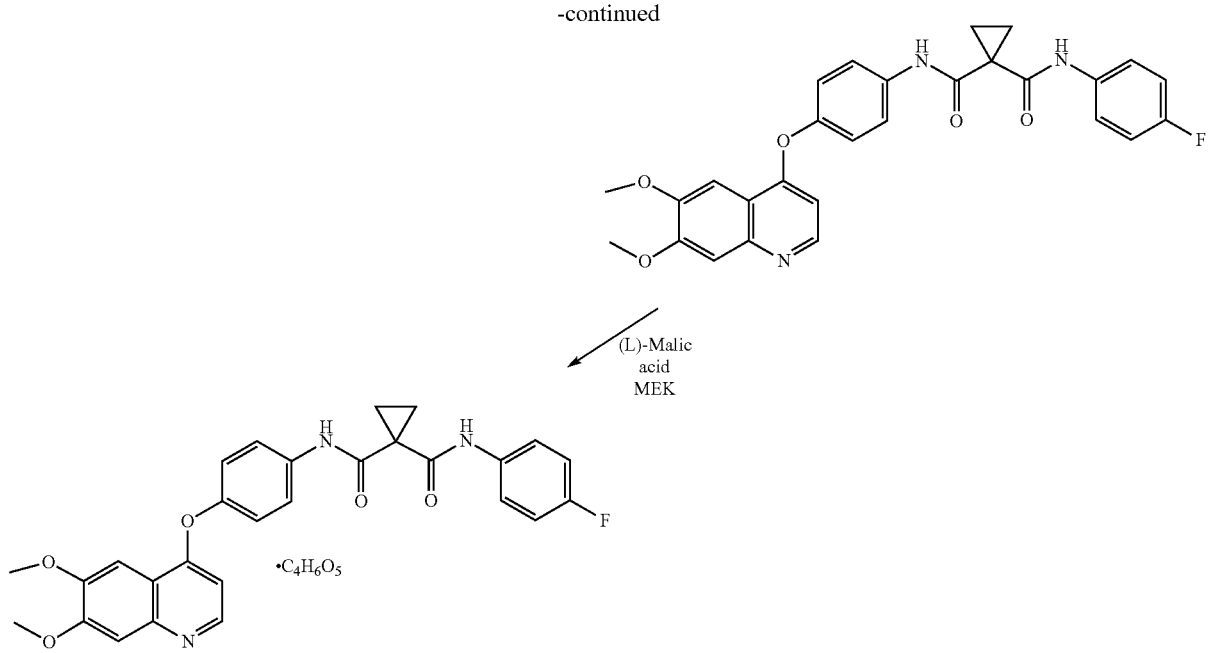

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl₃, 130.6 kg) was added. After the addition of POCl₃, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2-7° C. and then quenched into a chilled solution of dichloromethane (DCM, 482.8 kg), 26% NH₄OH (251.3 kg), and water (900 L). The resulting mixture was warmed to approximately 20-25° C., and phases were separated. The organic phase was filtered through a bed of AW hyflo super-eel NF (Celite; 5.4 kg) and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate which was then filtered and washed with n-heptane (92.0 kg), and dried on a filter at approximately 25° C. under nitrogen to afford the title compound. (35.6 kg).

Preparation of 4-(6,7-dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg) and DMA (167.2 kg) at 20-25° C. This mixture was then heated to 100-105° C. for approximately 13 hours. After the reaction was deemed complete as determined using in-process HPLC analysis (<2% starting material remaining), the reactor contents were cooled at 15 to 20° C. and water (pre-cooled, 2 to 7° C., 587 L) charged at a rate to maintain 15 to 30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0-5° C. and aged for approximately 1 h after which time the solid was filtered, washed with THF (147.6 kg) and dried on a filter under vacuum at approximately 25° C. to yield 4-(6,7-dimethoxy-quinoline-4-yloxy)-phenylamine (34.0 kg).

Alternative Preparation of 4-(6,7-dimethoxy-quinoline-4-yloxy)-phenylamine 4-chloro-6,7-dimethoxyquinoline (34.8 kg) and 4-aminophenol (30.8 kg) and sodium tert pentoxide (1.8 equivalents) 88.7 kg, 35 wt percent in THF) were charged to a reactor, followed by N,N-dimethylacetamide (DMA, 293.3 kg). This mixture was then heated to 105-115° C. for approximately 9 hours. After the reaction was deemed complete as determined using in-process HPLC analysis (<2% starting material remaining), the reactor contents were cooled at 15 to 25° C. and water (315 kg) was added over a two hour period while maintaining the temperature between 20 and 30° C. The reaction mixture was then agitated for an additional hour at 20 to 5° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used and the reaction temperature was increased from 110-120° C. In addition, the cool down temperature was increased to 35-40° C. and the starting temperature of the water addition was adjusted to 3540° C., with an allowed exotherm to 45° C.

Preparation of 1-(4-fluoro-phenylcarbamoyl)-cyclopropanecarboxylic acid

Triethylamine (19.5 kg) was added to a cooled (approximately 5 C) solution of cyclopropane-1,1-dicarboxylic acid (24.7 kg) in THF (89.6 kg) at a rate such that the batch temperature did not exceed 5° C. The solution was stirred for approximately 1.3 hours, and then thionyl chloride (23.1 kg) was added, keeping the batch temperature below 10° C. When the addition was complete, the solution was stirred for approximately 4 h keeping temperature below 10° C. A solution of 4-fluoroaniline (18.0 kg) in THF (33.1 kg) was then added at a rate such that the batch temperature did not exceed 10° C. The mixture was stirred for approximately 10 hours after which the reaction was deemed complete. The reaction mixture was then diluted with isopropyl acetate (218.1 kg). This solution was washed sequentially with aqueous sodium hydroxide (10.4 kg, 50% dissolved in 119 L of water) further diluted with water (415 L), then with water (100 L) and finally with aqueous sodium chloride (20.0 kg dissolved in 100 L of water). The organic solution was concentrated by vacuum distillation (100 L residual volume) below 40° C. followed by the addition of n-heptane (171.4 kg), which resulted in the precipitation of solid. The solid was recovered by filtration and washed with n-Heptane (102.4 kg) resulting in wet crude, 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C. followed by the addition of water (320 L) resulting in slurry which was recovered by filtration, washed sequentially with water (20 L) and n-heptane (103.1 kg) and then dried on the filter at approximately 25° C. under nitrogen to afford the title compound (25.4 kg).

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl chloride A reactor was charged with 1-(4-fluoro-phenylcarbamoyl)-cyclopropanecarboxylic acid (35 kg), 344 g DMF, and 175 kg THF. The reaction mixture was adjusted to 12-17° C. and then to the reaction mixture was charged 19.9 kg of oxalyl chloride over a period of 1 hour. The reaction mixture was left stirring at 12-17° C. for 3 to 8 hours. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide (Compound IA)

The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20-25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by 412.9 kg THF. To the reaction mixture was charged a solution of 48.3 $K_2CO_3$ in 169 kg water. The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20-30° C. over a minimum of two hours. The reaction mixture was stirred at 20-25° C. for a minimum of three hours. The reaction temperature was then adjusted to 30-25° C. and the mixture was agitated. The agitation was stopped and the phases of the mixture were allowed to separate. The lower aqueous phase was removed and discarded. To the remaining upper organic phase was added 804 kg water. The reaction was left stirring at 15-25° C. for a minimum of 16 hours.

The product precipitated. The product was filtered and washed with a mixture of 179 kg water and 157.9 THF in two portions. The crude product was dried under a vacuum for at least two hours. The dried product was then taken up in 285.1 kg THF. The resulting suspension was transferred to reaction vessel and agitated until the suspension became a clear (dissolved) solution, which required heating to 30-35° C. for approximately 30 minutes. 456 kg water was then added to the solution, as well as 20 kg SDAG-1 ethanol (ethanol denatured with methanol over two hours. The mixture was agitated at 15-25° C. for at least 16 hours. The product was filtered and washed with a mixture of 143 kg water and 126.7 THF in two portions. The product was dried at a maximum temperature set point of 40° C.

In an alternative procedure, the reaction temperature during acid chloride formation was adjusted to 10-15° C. The recrystallization temperature was changed from 15-25° C. to 45-50° C. for 1 hour and then cooled to 15-25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, (L) malate salt (Compound IB)

Cyclopropane-1,1-dicarboxylic acid [4-(6,7-dimethoxy-quinoline-4-yloxy)-phenyl]-amide (4-fluoro-phenyl)-amide (1-5; 13.3 kg), L-malic acid (4.96 kg), methyl ethyl ketone (MLEK; 188.6 kg) and water (37.3 kg) were charged to a reactor and the mixture was heated to reflux (approximately 74° C.) for approximately 2 hours. The reactor temperature was reduced to 50 to 55° C. and the reactor contents were filtered. These sequential steps described above were repeated two more times starting with similar amounts of 1-5 (13.3 kg), L-Malic acid (4.96 kg), MEK (198.6 kg) and water (37.2 kg). The combined filtrate was azeotropically dried at atmospheric pressure using MEK (1133.2 kg) (approximate residual volume 711 L; KF≤0.5% w/w) at approximately 74° C. The temperature of the reactor contents was reduced to 20 to 25° C. and held for approximately 4 hours resulting in solid precipitate which was filtered, washed with MEK (448 kg) and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2), 658.2 kg methyl ethyl ketone, and 129.1 kg water (37.3 kg) were charged to a reactor and the mixture was heated 50-55° C. for approximately 1-3 hours, and then at 55-60° C. for an addition al 4-5 hours. The mixture was clarified by filtration through a 1 μm cartridge. The reactor temperature was adjusted to 20-25° C. and vacuum distilled with a vacuum at 150-200 mm Hg with a maximum jacket temperature of 55° C. to the volume range of 558-731 L.

The vacuum distillation was performed two more times with the charge of 380 kg and 380.2 kg methyl ethyl ketone, respectively. After the third distillation, the volume of the batch was adjusted to 18 v/w of Cyclopropane-1,1-dicarboxylic acid [4-(6,7-dimethoxy-quinoline-4-yloxy)-phenyl]-amide (4-fluoro-phenyl)-amide by charging 159.9 kg methyl ethyl ketone to give a total volume of 880 L. An addition al vacuum distillation was carried out by adjusting 245.7 methyl ethyl ketone. The reaction mixture was left with moderate agitation at 20-25° C. for at least 24 hours. The product was filtered and washed with 415.1 kg methyl ethyl ketone in three portions. The product was dried under a vacuum with the jacket temperature set point at 45° C.

In an alternative procedure, the order of addition was changed so that a solution of 17.7 kg L-malic acid dissolved in 129.9 kg water was added to Cyclopropane-1,1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Preparation of Compound IB, Form N-1

A solution was prepared by adding tetrahydrofuran (12 mL/g-bulk-LR (limiting reagent); 1.20 L) and N-(4-{[6,7-bis(methyloxy)-quinolin-4-yl]oxy}phenyl)-N'-(4-fluorophenyl)cyclopropane-1,1-dicarboxamide, (100 g; 1.00 equiv; 100.00 g) and (L)-malic acid (1.2 equiv (molar); 32.08 g) to a 1 L reactor. Water (0.5317 mL/g-bulk-LR; 53.17 mL) was added and the solution was heated to 60° C. and maintained at that temperature for one hour until the solids were fully dissolved. The solution was passed through a Polish Filter.

At 60° C., acetonitrile (12 mL/g-bulk-LR; 1.20 L) was added over a period of 8 hours. The solution was held at 60° C. for 10 hours. The solution was then cooled to 20° C. and held for 1 hour. The solids were filtered and washed with acetonitrile (12 mL/g-bulk-LR; 1.20 L). The solids were dried at 60° C. (25 mm Hg) for 6 hours to afford compound (I), Form N-1 (108 g; 0.85 equivalent; 108.00 g; 85.22% yield) as a white crystalline solid.

Alternate Preparation of Compound IB, Form N-1

A solution was prepared with 190 mL tetrahydrofuran (110 mL), methyl isobutyl ketone, and 29 mL water. Next, 20 mL of this solution were transferred into an amber bottle, and then saturated by adding N-(4-{[6,7-bis(methyloxy)-quinolin-4-yl]oxy}phenyl)-N'-(4-fluorophenyl)cyclopropane-1,1-dicarboxamide, (L)-malate until a thick slurry formed, and aging for at least 2 hours with stirring at room temperature. The solids were removed by filtration through a Buchner funnel, rendering a clear saturated solution.

Separately, a powder blend was made with known amounts of two batches of compound IB: (1) 300 mg of batch 1, which contained approximately 41% compound IB, Form N-1 and 59% compound IB, Form N-2 by Raman spectroscopy analysis, and (2) 200 mg of batch 2, which had a XPRD pattern similar to compound IB, Form N-2.

The compound IB, Form N-1 and compound (I), Form N-2 powder blend was added into the saturated solution, and the slurry was aged under magnetic stirring at room temperature for 25 days. The slurry was then sampled and filtered through a Buchner funnel to obtain 162 mg of wet cake. The wet cake was dried in a vacuum oven at 45° C. to afford 128 mg of crystalline compound IB in the N-1 form.

Preparation of Crystalline Compound IB, Form N-2

Preparation of Crystalline Compound IB, Form N-2 Seed Crystals

A solution was prepared by combining 20 ml of acetone and 300 mg of compound IA (N-(4-{[6,7-bis(methyloxy)quinolin-4-yl]oxy}phenyl)-N'-(4-fluorophenyl)cyclopropane-1,1-dicarboxamide) in a 25 ml screw capped vial. Next, 0.758 ml of a 0.79M (L)-malic acid stock solution was added to the vial with magnetic stirring. The solution was then left stirring for 24 hours at ambient temperature. The sample was then suction filtered with 0.45 μm PTFE filter cartridge and dried in vacuo at ambient temperature overnight.

Preparation of Crystalline Compound IB, Form N-2.

To a reactor were added N-(4-{[6,7-bis(methyloxy)-quinolin-4-yl]oxy}phenyl)-N'-(4-fluorophenyl)cyclopropane-1,1-dicarboxamide (48 g; 1.00 equiv; 48.00 g) and tetrahydrofuran (16.5 mL/g-bulk-LR; 792.00 mL). The water content was adjusted to 1 wt % water. The solution was heated to 60° C. Once dissolved, the solution was passed through a polish filter to provide the first solution.

In a separate reactor, (L)-malic acid (1.2 equiv (molar); 15.40 g) was dissolved into methyl isobutyl ketone (10 mL/g-bulk-LR; 480.00 mL) and tetrahydrofuran (1 mL/g-bulk-LR; 48.00 mL). Next, 50 mL of the (L)-malic acid solution was added to the first solution at 50° C. Seed crystals were added (1%, 480 mg) and the malic acid solution was added at 50° C. dropwise via an addition funnel (1.3 ml/min over 3 hours). The slurry was held at 50° C. for 18 hours and then was cooled to 25° C. over 30 minutes. The solids were filtered, and washed with 20% tetrahydrofuran/methyl isobutyl ketone (10V, 480 mL). The solids were dried under vacuum at 60° C. for 5 hours to afford compound IB (55.7 g; 0.92 equivalent; 55.70 g; 91.56% yield) as an off-white crystalline solid.

Stability Studies of Pharmaceutical Compositions

The pharmaceutical capsule compositions of Tables 3 and 4 were prepared by mixing the ingredients according to processes known in the art.

TABLE 3

| Ingredient | mg/unit dose |
|---|---|
| Compound IB (10% drug load as Compound IA) | 25 |
| Microcrystalline Cellulose | 196.75 |
| Croscarmellose sodium | 12.5 |
| Sodium starch glycolate | 12.5 |
| Fumed Silica | 0.75 |
| Stearic acid | 2.5 |
| Total Fill Weight | 250 |

TABLE 4

| Ingredient | mg/unit dose |
|---|---|
| Compound IB (50% drug load as Compound IA) | 100 |
| Silicified Microcrystalline Cellulose | 75.40 |
| Croscarmellose sodium | 10.00 |
| Sodium Starch Glycolate | 10.00 |
| Fumed silica | 0.6 |
| Stearic Acid | 4.0 |
| Total Fill Weight | 200 |

The capsule compositions were subjected to stability studies to monitor the formation of 6,7-dimethoxy-quinoline-4-ol at various temperatures and relative humidities over time. The results are summarized in Tables 7A and 7B and Tables 8A and 8B.

TABLE 7A

Stability of 25 Mg Capsules (Table 3)

| | Conditions | Bottle A1 | Bottle A2 | Bottle A3 | Bottle A4 |
|---|---|---|---|---|---|
| | | PPM of 6,7-dimethoxy-quinoline-4-ol | | | |
| Initial T = 0 | 25° C./60% RH | 2 | 2 | 3 | 3 |
| 1 Month | 25° C./60% RH | 3 | 4 | 5 | NA |
| | 30° C./75% RH | 4 | 4 | NA | NA |
| | 40° C./75% RH | 9 | 9 | 10 | NA |
| 3 Months | 25° C./60% RH | 5 | 5 | 7 | NA |
| | 30° C./75% RH | 7 | 6 | NA | NA |
| | 40° C./75% RH | 22 | 23 | 24 | NA |
| 6 Months | 25° C./60% RH | 6 | 6 | 7 | 7 (3M in blister) |
| | 30° C./75% RH | 9 | 9 | NA | NA |
| | 40° C./75% RH | 40 | 44 | 43 | 27 (3M in blister) |
| 9 Months | 25° C./60% RH | 7 | 7 | 9 | 8 (6M in blister) |
| | 30° C./75% RH | 13 | 12 | NA | NA |
| | 40° C./75% RH | NA | NA | 68 | 60 (6M in blister) |

M = Months;
NA = Not Applicable;
RH = Relative Humidity;
PPM = Parts per Million.
A portion of Bottle A4 was repackaged in a blister pack after being stored in bottles for 3 months.

TABLE 7B

Stability of 25 Mg Capsules (Table 3)

| | Conditions | Bottle B1 | Bottle B | Bottle B3 | Bottle B4 |
|---|---|---|---|---|---|
| | | PPM of 6,7-dimethoxy-quinoline-4-ol | | | |
| Initial T = 0 | 25° C./60% RH | 3 | 1 | 2 | 2 |
| 1 Month | 25° C./60% RH | <2 | <2 | <2 | NA |
| | 30° C./75% RH | <2 | <2 | NA | NA |
| | 40° C./75% RH | 2 | <2 | <2 | NA |
| 3 Months | 25° C./60% RH | 2 | <2 | <2 | NA |
| | 30° C./75% RH | 2 | <2 | NA | NA |
| | 40° C./75% RH | 3 | <2 | <2 | NA |
| 6 Months | 25° C./60% RH | <2 | <2 | <2 | <2 (3M in blister) |
| | 30° C./75% RH | 2 | <2 | NA | NA |
| | 40° C./75% RH | 4 | <2 | 3 | 3 (3M in blister) |
| 9 Months | 25° C./60% RH | <2 | <2 | <2 | <2 (6M in blister) |
| | 30° C./75% RH | 3 | <2 | NA | NA |
| | 40° C./75% RH | NA | NA | 5 | 4 (6M in blister) |

A portion of Bottle B4 was repackaged in a blister pack after being stored in bottles for 3 months.

TABLE 8A

Stability of 100 Mg Capsules (Table 4)

| | Conditions | Bottle A1 | Blister A2 | Bottle A3 |
|---|---|---|---|---|
| | | PPM of 6,7-dimethoxy-quinoline-4-ol | | |
| Initial T = 0 | 25° C./60% RH | 4 | 4 | 6 |
| 1 Month | 25° C./60% RH | 4 | 4 | 6 |
| | 30° C./75% RH | 4 | NA | 6 |
| | 40° C./75% RH | 6 | 6 | 9 |
| 3 Months | 25° C./60% RH | 5 | 5 | 7 |
| | 30° C./75% RH | 6 | NA | 7 |
| | 40° C./75% RH | 10 | 10 | 12 |
| 6 Months | 25° C./60% RH | 5 | 5 | |
| | 30° C./75% RH | 6 | NA | |
| | 40° C./75% RH | 11 | 17 | |

M = Months;
NA = Not Applicable;
RH = Relative Humidity;
PPM = Parts per Million.

TABLE 8B

Stability of 100 Mg Capsules (Table 4)

| | Conditions | Bottle B1 | Blister B2 | Bottle B3 |
|---|---|---|---|---|
| | | PPM of 6,7-dimethoxy-quinoline-4-ol | | |
| Initial T = 0 | 25° C./60% RH | 1 | 1 | 2 |
| 1 Month | 25° C./60% RH | <2 | <2 | <2 |
| | 30° C./75% RH | <2 | <2 | 2 |
| | 40° C./75% RH | <2 | <2 | 2 |
| 3 Months | 25° C./60% RH | <2 | <2 | <2 |
| | 30° C./75% RH | <2 | NA | <2 |
| | 40° C./75% RH | <2 | <2 | 2 |
| 6 Months | 25° C./60% RH | <2 | <2 | |
| | 30° C./75% RH | <2 | NA | |
| | 40° C./75% RH | 2 | 2 | |

M = Months;
NA = Not Applicable;
RH = Relative Humidity;
PPM = Parts per Million.

The results summarized in Tables 7A and 7B and 8A and 8B indicate that formation of 6,7-dimethoxy-quinoline-4-ol was minimized to 50 ppm or less over time in the capsule formulations.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All references cited herein are incorporated by reference in their entirety.

The invention claimed is:

1. A pharmaceutical composition for oral administration comprising Compound IB:

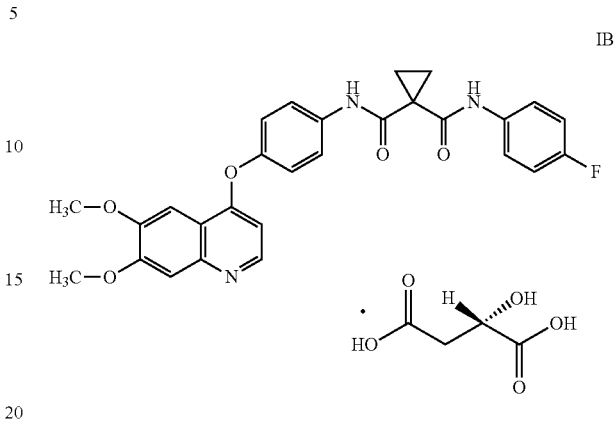

and a pharmaceutically acceptable carrier, wherein the pharmaceutical composition is a tablet or a capsule, and wherein the pharmaceutical composition contains 100 ppm or less of 6,7-dimethoxy-quinoline-4-ol.

2. The pharmaceutical composition of claim 1, wherein the pharmaceutical composition contains 50 ppm or less of 6,7-dimethoxy-quinoline-4-ol.

3. The pharmaceutical composition of claim 2, wherein the pharmaceutical composition contains 25 ppm or less of 6,7-dimethoxy-quinoline-4-ol.

4. The pharmaceutical composition of claim 3, wherein the pharmaceutical composition contains 10 ppm or less of 6,7-dimethoxy-quinoline-4-ol.

5. The pharmaceutical composition of claim 4, wherein the pharmaceutical composition contains 5 ppm or less of 6,7-dimethoxy-quinoline-4-ol.

6. A method of treating cancer, comprising administering to a subject in need thereof a pharmaceutical composition comprising Compound IB:

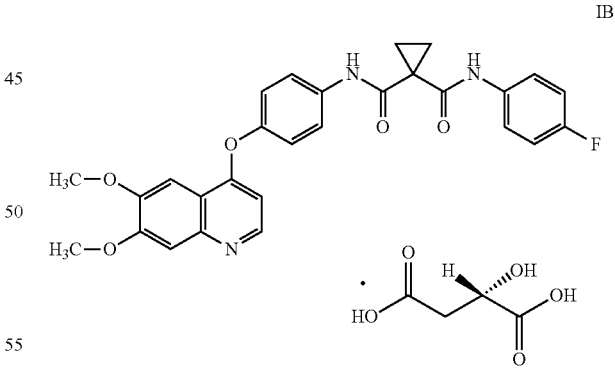

and a pharmaceutically acceptable carrier, wherein the pharmaceutical composition is a tablet or a capsule, and wherein the pharmaceutical composition contains 100 ppm or less of 6,7-dimethoxy-quinoline-4-ol.

7. The method of claim 6, wherein the pharmaceutical composition contains 50 ppm or less of 6,7-dimethoxy-quinoline-4-ol.

8. The method of claim 7, wherein the pharmaceutical composition contains 25 ppm or less of 6,7-dimethoxy-quinoline-4-ol.

9. The method of claim 8, wherein the pharmaceutical composition contains 10 ppm or less of 6,7-dimethoxy-quinoline-4-ol.

10. The method of claim 9, wherein the pharmaceutical composition contains 5 ppm or less of 6,7-dimethoxy-quinoline-4-ol.

11. The method of claim 6, wherein the cancer is renal cancer.

12. The method of claim 6, wherein the cancer is prostate cancer.

13. The method of claim 6, wherein the cancer is hepatocellular carcinoma.

14. The method of claim 7, wherein the cancer is renal cancer.

15. The method of claim 7, wherein the cancer is prostate cancer.

16. The method of claim 7, wherein the cancer is hepatocellular carcinoma.

17. The method of claim 8, wherein the cancer is renal cancer.

18. The method of claim 8, wherein the cancer is prostate cancer.

19. The method of claim 8, wherein the cancer is hepatocellular carcinoma.

20. The method of claim 9, wherein the cancer is renal cancer.

21. The method of claim 9, wherein the cancer is prostate cancer.

22. The method of claim 9, wherein the cancer is hepatocellular carcinoma.

* * * * *